(12) United States Patent
Munro, III

(10) Patent No.: US 6,709,381 B2
(45) Date of Patent: Mar. 23, 2004

(54) BRACHYTHERAPY SYSTEMS AND METHODS

(75) Inventor: John J. Munro, III, North Androver, MA (US)

(73) Assignee: Implant Sciences Corporation, Wakefield, MA (US)

( * ) Notice: Subject to any disclaimer, the term of this patent is extended or adjusted under 35 U.S.C. 154(b) by 0 days.

(21) Appl. No.: 10/160,881

(22) Filed: May 31, 2002

(65) Prior Publication Data

US 2002/0177748 A1 Nov. 28, 2002

Related U.S. Application Data

(63) Continuation-in-part of application No. 10/118,415, filed on Apr. 8, 2002, now abandoned.
(60) Provisional application No. 60/290,108, filed on May 10, 2001.

(51) Int. Cl.[7] .............................. A61N 5/00; A61B 5/00
(52) U.S. Cl. ............................................ 600/3; 600/585
(58) Field of Search .................................. 600/1–8, 585, 600/433; 376/158, 202; 604/164.01; 424/1.29, 422; 534/697, 696, 700, 703, 710, 711, 722, 723; 251/124

(56) References Cited

U.S. PATENT DOCUMENTS

| | | | |
|---|---|---|---|
| 4,323,055 A | 4/1982 | Kubiatowicz | 128/1.2 |
| 4,510,924 A | 4/1985 | Gray | 128/1.2 |
| 4,763,642 A | 8/1988 | Horowitz | 128/1.2 |
| 4,784,116 A | 11/1988 | Russell, Jr. et al. | 128/1.2 |
| 4,815,449 A | 3/1989 | Horowitz | 600/7 |
| 4,891,165 A | 1/1990 | Suthanthiran | 252/633 |
| 4,994,013 A | 2/1991 | Suthanthiran et al. | 600/8 |
| 5,141,487 A * | 8/1992 | Liprie | 600/7 |
| 5,395,300 A * | 3/1995 | Liprie | 600/3 |
| 5,405,309 A | 4/1995 | Carden, Jr. | 600/3 |
| 6,010,446 A | 1/2000 | Grimm | 600/3 |
| 6,074,337 A * | 6/2000 | Tucker et al. | 600/2 |
| 6,099,458 A | 8/2000 | Robertson | 600/8 |
| 6,203,485 B1 * | 3/2001 | Urick | 600/3 |
| 6,221,003 B1 * | 4/2001 | Sierocuk et al. | 600/7 |
| 6,231,494 B1 * | 5/2001 | Verin et al. | 600/1 |
| 6,248,057 B1 | 6/2001 | Mavity et al. | 600/3 |
| 6,264,598 B1 | 7/2001 | Armini | 600/3 |
| 6,264,600 B1 * | 7/2001 | Grimm | 600/7 |
| 6,273,851 B1 * | 8/2001 | Slater et al. | 600/8 |
| 6,450,939 B1 * | 9/2002 | Grimm | 600/8 |
| 6,497,647 B1 * | 12/2002 | Tucker | 600/8 |

* cited by examiner

Primary Examiner—Eric F. Winakur
Assistant Examiner—Nikita R. Veniaminov
(74) Attorney, Agent, or Firm—Choate, Hall & Stewart

(57) ABSTRACT

A system for brachytherapy is provided. The system includes an implantation device having a tubular member, a radioactive source within the member, and a socket at opposing ends of the tubular member. A plurality of implantation devices may be joined into an assembly by use of a spacer positioned within the sockets of adjoining devices. The device may be deployed at an implantation site by use of a delivery mechanism, such as needle. The presence of the tubular members and spacers minimizes movement of the radioactive source subsequent to deployment, so as not to alter dose distribution for subsequent irradiation.

24 Claims, 2 Drawing Sheets

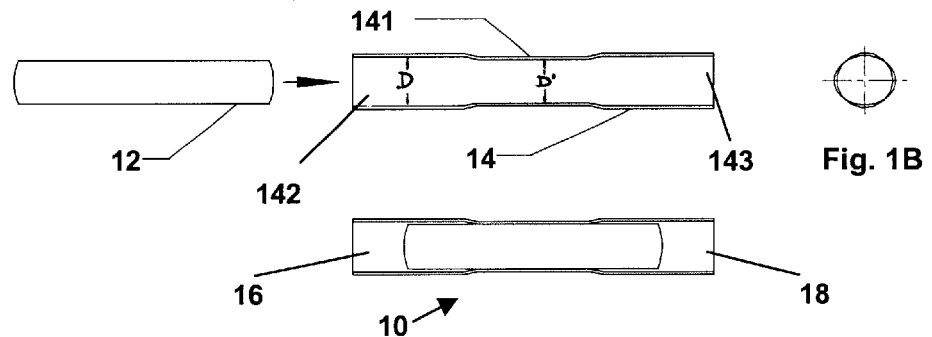
Fig. 1A
Fig. 1B
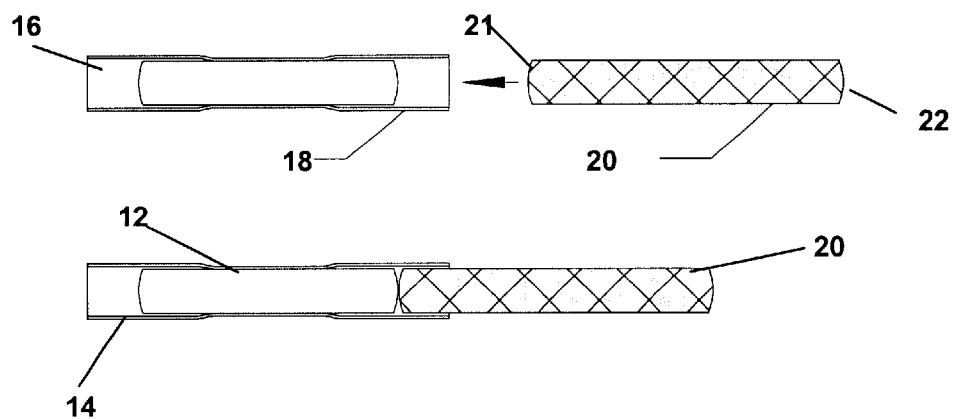
Fig. 2
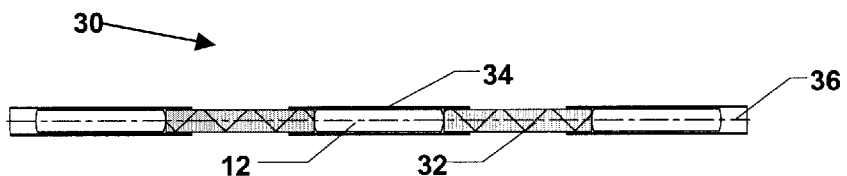
Fig. 3

BRACHYTHERAPY SYSTEMS AND METHODS

RELATED U.S. APPLICATION(S)

This application is a continuation-in-part of U.S. application Ser. No. 10/118,415, filed Apr. 8, 2002, now abandonded which application claims priority to U.S. Provisional Application Serial No. 60/290,108, filed May 10, 2001. Both applications are hereby incorporated herein by reference.

FIELD OF THE INVENTION

The present invention relates to implantable devices, and in particular, to implantable devices for radiation therapy.

BACKGROUND ART

Ionizing radiation is employed in the management of a wide variety of malignant tumors, providing a mechanism whereby the malignancy can be destroyed while the normal tissues are preserved. With preservation of normal tissues, normal function and normal appearance may also be preserved. Hence, ionizing radiation forms part of the treatment for over half of all patients with cancer. The overall effectiveness of radiation therapy, however, depends upon the balance between effective tumor control and morbidity due to the treatment. It is understood that the differential effects of ionizing radiation on tumors and normal tissues gives rise to a favorable therapeutic ratio for most patients. However, radiation can have destructive immediate and delayed effects on normal tissues. Techniques employed for radiation therapy significantly affect the incidence and severity of these destructive effects.

Because all types of ionizing radiation affect tissues via the same basic physical mechanisms, differences in spatial or temporal distributions are responsible for different effects observed with equal physical doses. The method for delivering radiation thus becomes highly significant. Treatment modalities for delivering therapeutic ionizing radiation include external beam radiation and direct placement of radioactive sources within tissues. This latter technique, termed brachytherapy, may permit delivery of ionizing radiation to a tumor in higher doses than those achievable with external beam radiation. Conventional external beam radiation treatments rely on multiple fractions of dose in order to ensure that the highest fractions of tumor cells are exposed at the most sensitive parts of the cell life cycle. Brachytherapy implants, such as brachytherapy seeds, on the other hand, can supply a continuous and highly localized radiation dose to the surrounding tissue. Because a delivered dose from a radiation source decreases proportionately to the square of the distance from that source, brachytherapy permits the delivery of very high radiation doses to those areas of a tumor in close proximity to the implant, with relative sparing of more distant tissues. With careful placement, so that the radiation source is in proximity to the tumor and distant from normal tissue, effective therapy against the tumor may be combined with minimal collateral damage to normal tissues. A variety of radioisotopes, including $^{125}$Iodine, $^{103}$Palladium, $^{137}$Cesium, and $^{192}$Iridium, may be used in the treatment of cancers involving such tissues as the breast, the prostate, the brain, along, the head and neck, the female reproductive tract, the musculoskeletal system and related soft tissues, and the eye.

As understood herein, those radioactive sealed sources employed in brachytherapy implants will be termed "seeds." Commonly, seeds are intended for permanent implantation. A description of certain types of seeds can be found in B H Heintz et al., "Comparison of I-125 sources used for permanent interstitial implants," Medical Physics, Vol. 28, No. 4, p. 673 (April 2001), the contents of which are hereby incorporated by reference. Certain devices known in the prior art are intended for insertion directly into the tissues without employing a needle or other similar delivery device. An example of such a device may be found in the disclosure of U.S. Pat. No. 4,815,449. This patent provides, in certain embodiments, an implant of sufficient rigidity to be driven into a tumor without deflection, so that the implant may be used independently of a positioning or delivery device.

Alternatively, brachytherapy seeds may be positioned in the tissues to be treated by insertion through a delivery device, for instance, a needle. Using a delivery device may allow more precise positioning of seeds in areas requiring treatment. Brachytherapy seeds from various manufacturers may be made to the same set of specifications so that they are compatible with those delivery systems in common use. In those delivery systems, the seeds may be preloaded into needles or other delivery devices. The position of a plurality of seeds within the delivery device may be maintained by placing loose spacers between the seeds to establish and maintain a desired positioning. Once the seeds are positioned in the delivery device, insertion into the tissues takes place. To insert the seeds, the needle containing them must first be inserted to a preselected depth into the appropriate position in the patient's tissues. An injection mechanism such as a mandrel may then be inserted into the needle with its distal end in contact with the seeds. The needle, thereafter, may be withdrawn over the mandrel, leaving the seeds and loose spacers resident in the preselected tissue area. Once positioned within the tissues using this method, the seeds and loose spacers are free to move from their original position, as there are no constraints on the position or orientation of the seeds. This can lead to the undesirable consequence that dose distribution within the tissue may be changed. For instance, movement of the seeds after deployment can change the area being irradiated, and can change the dose being delivered both to the preselected tumor regions and to the surrounding normal tissues.

There remains, therefore, a need for a system that can retain the brachytherapy seeds in position relative to one another prior to delivery, and which can retain the position of the brachytherapy seeds in relation to the tumor after the seeds are delivered into the tissues.

SUMMARY OF THE INVENTION

The present invention provides, in one embodiment, an implantable device for radiation therapy of pathological tissues. The device, in an embodiment, includes a substantially tubular member having opposing ends, a central section into which a radioactive sealed source is positioned between the ends, and a socket at each of the opposing ends. The device further includes a spacer partially positioned within one of the sockets, such that the blunt end on the spacer is exposed.

In another embodiment of the invention, an assembly of a plurality of tubular members, each having opposing ends, a central section into which a radioactive sealed source is positioned between the opposing end and a socket at each of the opposing ends. The assembly further includes a spacer positioned between two tubular members, such that the spacer is partially retained within one socket of each tubular member, to permit joining of the tubular members in series along a common axis.

In a further embodiment, the invention provides a method for manufacturing a brachytherapy implant. The method includes providing a tubular member having opposing ends, a central section positioned between the opposing ends, into which is placed a radioactive sealed source, thereby creating a socket at each of the opposing ends. Next, a spacer may be placed within a socket and subsequently secured therein. A second spacer may be placed in the opposing socket and subsequently secured therein.

A method of treating pathological tissues is also provided in accordance with an embodiment of the present invention. Initially, a site of pathological tissues is identified. Next, an implantable device is provided. The device, in one embodiment, includes at least one substantially tubular member having opposing ends, a central section into which a radioactive sealed source is positioned between the opposing ends, a socket at each of the opposing ends. The device, in another embodiment, includes at least one spacer positioned within one of the sockets of the device. The device can thereafter be placed within a lumen of a delivery mechanism. Once the implantable device is placed within the lumen, the delivery mechanism can be inserted at the site having the pathological tissues to a depth that permits access to the pathological tissues. Subsequently, the implantable device can be delivered from the lumen of the delivery mechanism to the site of the pathological tissues.

The device, in another embodiment, includes a spacer that is echogenic, enhancing the ultrasonic visibility of the spacer and, indirectly, enhancing the determination of the location of the attached radioactive sealed source.

BRIEF DESCRIPTIONS OF THE DRAWINGS

FIGS. 1A–B illustrate an implantable device in accordance with one embodiment of the present invention.

FIG. 2 illustrates a spacer for use in connection with the device illustrated in FIGS. 1A–B.

FIG. 3 illustrates an assembly of implantable devices in accordance with an embodiment of the present invention.

Figure 4A:
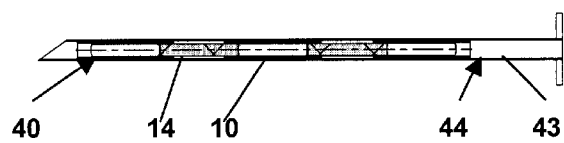
Figure 4B:
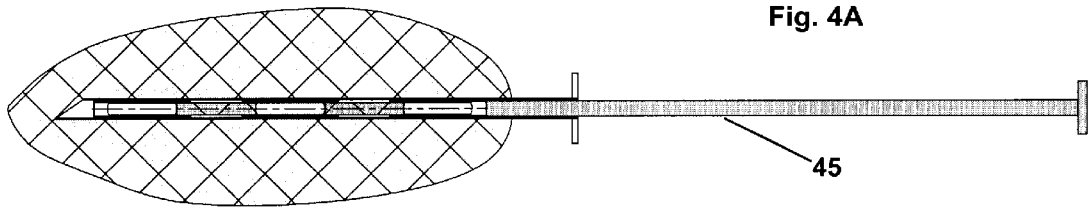
Figure 4C:
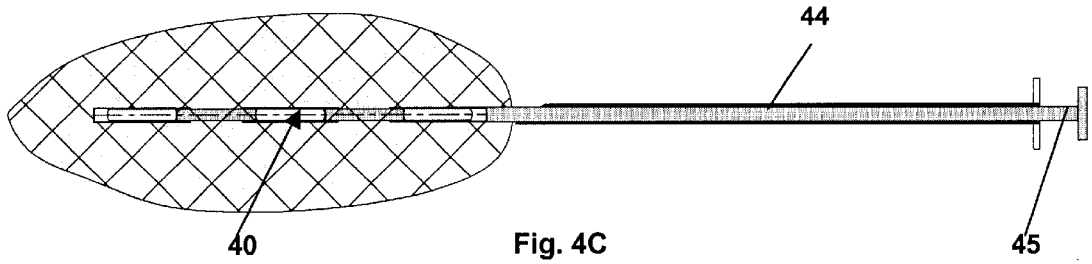
Figure 4D:
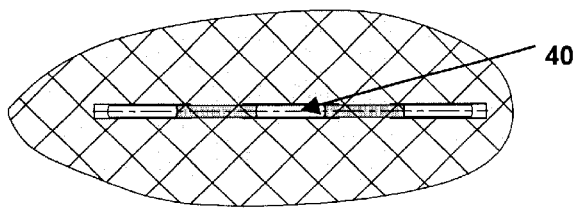

FIGS. 4A–D illustrate a method for implanting the device, in accordance with one embodiment of the present invention.

DETAILED DESCRIPTION OF SPECIFIC EMBODIMENTS

FIGS. 1A–B illustrate an implantable device 10 for radiation therapy of pathological tissues, for example, a tumor, through the use of a delivery device, such as a needle. As shown FIG. 1A, the device 10 includes, in accordance with one embodiment of the present invention, a substantially tubular member 14, a radioactive source, such as seed 12, positioned within the tubular member 14, and opposing sockets 16 and 18 defined by a difference in length between the seed 12 and the tubular member 14.

Still looking at FIG. 1A, the tubular member 14 includes a central section 141 positioned between opposing ends 142 and 143, and within which seed 12 may be placed. The central section 141, in one embodiment, may include an inner diameter D' that is slightly smaller than inner diameter D for the remainder of the member 14. In this manner, the central section 141 can provide resistance to longitudinal displacement of the seed 12. To provide the central section 141 with inner diameter D', the central section 141 may be crimped or otherwise deformed by methods known in the art. Alternatively, an adhesive, such as a biocompatible cement, may be used at the central section 141 to create an area of bonding between a portion of the external surface of the seed 12 and a portion of the interior surface of the tubular member 14 to provide resistance to longitudinal displacement of the seed within the member 14. The use of an adhesive may be without a crimped central section 141 or may be use with the crimped central section 141.

The seed 12 for use in connection with the tubular member 14 of the present invention may be manufactured, in one embodiment, from a variety of radioisotopes, including iodine-125, palladium-103, cesium-137, and iridium-192. Moreover, seed 12 is preferably radioactively sealed to prevent the radioactive material within itself from contacting tissues or with bodily fluids. The seeds for use with the tubular member 14 may also be obtained commercially, for instance, seed model 3500 manufactured by Implant Sciences Corporation of Wakefield, Mass., or may be any other seed model familiar to those skilled in the art. As illustrated in FIG. 1A seed 12 may be provided with a diameter that is substantially the same as the inner diameter D' of the central section 141 to permit a sufficient friction fit therein. However, it should be understood that various dimensions and configurations of the seeds may be employed in accordance with the therapeutic demands of a particular clinical situation.

In accordance with one embodiment of the present invention, the tubular member 14 may include an inner diameter D of about 0.8 millimeters (mm), suitable for accommodating a brachytherapy seed, and an outer diameter OD of about 1.0 mm, suitable for unobstructed passage through an interior channel (i.e., lumen) of a needle (FIGS. 4A–C) or other delivery devices employed in the implantation of brachytherapy seeds into a patient. For example, an 18 gauge needle, suitable for implant delivery, is understood to have an interior channel with a diameter of about 1.05 mm, which diameter should provide sufficient clearance for the tubular member 14 to pass therethrough. In addition, the tubular member 14 preferably is of a length that is suitable to accommodate seed 12. In one embodiment, the tubular member 14 may be provided with a length of approximately 9.5 to 10.0 millimeters (mm) or slightly longer, while the seed 12 may be provided with a length of about 5.5 mm. It should be appreciated that the inner diameter D, the outer diameter OD, and the central section 22 can be manufactured with different dimensions to accommodate the type of treatment to be performed.

The tubular member 14 may be fabricated, in accordance with an embodiment, by injection molding or by similar processes. Alternatively, the tubular member 14 may be manufactured by an extrusion method, dip-casting, or other processes familiar to those skilled in the art. In dip-casting, a metal rod may be dipped into a viscous solution to coat the surface of the rod. Subsequently, after drying, the coating on the metallic rod can be pulled off to provide tubular member 14. As the tubular member 14 will be manipulated during implantation, it may be desirable to fabricate the tubular member from a strong material, for example, titanium.

As illustrated in FIG. 1A, opposing sockets 16 and 18 are defined by a difference in length between the seed 12 and the tubular member 14. The opposing sockets 16 and 18, in an embodiment, are adapted so that each can receive and retain a portion of a spacer 20 (FIG. 2). In this manner sockets 16 and 18 may be provided with an inner diameter which can securely receive a seed 12 or 18 therein. In the embodiment shown in FIG. 1A, the diameter of each socket is substantially similar to the inner diameter D of the tubular member 14. It should be noted that, although illustrated in FIG. 1B as circular, each socket may be provided with a diameter and a circumferential profile of any geometrical pattern, so long as the spacer 20 can be securely positioned within the socket. If desired, the opposing sockets 16 and 18 may be provided with similar inner diameters and/or circumferential profiles, or with different inner diameters and/or circumferential profiles.

With reference now to the spacer 20, as shown in FIG. 2, the spacer 20 is substantially elongated and includes a proximal end 21 and a distal end 22. The proximal end 21 is typically received within the sockets of tubular member 14. The exposed distal end 22, on the other hand, may be rounded or blunted, so that trauma to surrounding tissues can be minimized during and subsequent to the implantation of the device 10. In an embodiment of the invention, both the distal end 21 and proximal end 22 can be rounded or blunted, so that regardless of which end is within a socket of tubular member 14, the remaining exposed portion of the spacer 20 includes a blunt end.

The spacer 20, in one embodiment of the invention, may be provided with a length that is suitable to position the seed 12 at a spacing suitable for the desired treatment. In an embodiment, the spacer 20 may be made to include a length that is approximately 5.5 mm, and a diameter that is approximately 0.8 mm to provide seed spacing between tubular members that is approximately 10.0 mm on center. It should be appreciated that the spacer 20 of the present invention can be manufactured with different dimensions to accommodate the type of treatment to be performed.

Moroeover, as the spacer 20 is designed for delivery and placement within tissues through a delivery device, it may be obtained commercially or may be made from a flexible material. In one embodiment of the present invention, the spacer 20 may be made from a bioresorbable polymer, such as poly-(L-lactide), poly-(DL-lactide), polyglycolide, or any other bioresorbable polymer known to those skilled in the art. In certain embodiments, the polymeric formulation may be chosen, so that the absorption thereof would be minimal over a certain period, for example, from about 60 to about 120 days, with substantially complete absorption thereof in about a year.

The spacer 20 may be fabricated, in accordance with an embodiment, as a single piece by extrusion, injection molding or by similar processes to permit joining of multiple tubular members 14. In addition, as it may be desired to identify the location of the spacer 20, and the tubular member 14 along with the seed 12 within the tissue during or after implantation, the spacer 20 may be fabricated in such a way as to enhance its visibility under ultrasonic examination. In one embodiment, the spacer 20 may be made to include voids or gas pockets during the fabrication process.

The spacer 20 may be affixed to the opposing sockets 16 and 18 by the use of, for instance, a friction-fit, biocompatible cement, bioresorbable cement, or by any other affixation method known in the art. Of course, the spacer 20 need not be sealed within the socket 16 or 18, as the seed 12 is itself sealed to prevent contact of the radioactive material within the seed 12 with bodily fluids.

Referring now to FIG. 3, the device 10 may be joined with a plurality of other devices 10 to provide an assembly 30. As illustrated, additional spacers 32 may be added to the assembly 30 by positioning an existing exposed distal end of the spacer 32 within a socket 36 of a new tubular member 34. Depending on the situation and the treatment required, the assembly 30 may include a spacer 32 at each end of the assembly, one spacer 32 at an end of the assembly with the other end empty leaving an exposed socket, or no seed at either end of the assembly 30. Affixation of the spacer 32 to the tubular member 14 may be accomplished by employing the means provided above.

To treat pathological tissues, looking now at FIGS. 4A–D, an assembly 40 of spacers 41 and devices 10 may be fabricated and positioned within a lumen 43 of a delivery device, such as a needle 44. The needle 44, subsequently, can be placed at a site selected for implantation and inserted to a preselected depth, so as to permit the needle to access the pathological tissues. An injection mechanism, such as a mandrel 45, can then be inserted into the needle 44 until its distal end contacts the assembly 40. The needle 44 may, thereafter, be withdrawn over the mandrel 45, leaving the assembly 40 at the site of implantation. The presence of the spacers 41 prevents the plurality of devices 10 from substantially moving away from the initial site of implantation, so as not to alter the dose distribution within the tissue for subsequent irradiation.

Alternatively, the site selected for implantation can initially be surgically exposed. Thereafter, the assembly 40 can be placed within the exposed site. Once the assembly 40 has been securely positioned within the site, the site may be closed by suturing to retain the assembly 40 therein.

It should be understood that although an assembly is discussed in connection with the treatment of pathological tissues, a single implantation device 10 may be used.

While the invention has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. An implantable device for radiation therapy comprising:
   a substantially tubular member having opposing ends and a central section positioned between the opposing ends;
   a sealed radioactive source positioned within the tubular member at the central section; and
   a socket at each of the opposing ends, the sockets being defined by a difference in length between the tubular member and the radioactive source, wherein at least one socket is open to the sealed radioactive source.

2. A device as set forth in claim 1, wherein the central section includes a diameter that is smaller than that of the remainder of tubular member to provide resistance to longitudinal displacement of the radioactive source.

3. A device as set forth in claim 2, wherein the central section is crimped to provide resistance to longitudinal displacement of the radioactive source.

4. A device as set forth in claim 1, wherein the central section includes an adhesive along its interior surface to permit bonding of the radioactive source thereto to provide resistance to longitudinal displacement of the radioactive source.

5. A device as set forth in claim 1, wherein each of the sockets includes an inner diameter sufficiently sized to securely retain the radioactive source therein.

6. A device as set forth in claim 1, wherein each of the sockets includes a depth sufficient to retain a portion of a spacer.

7. A device as set forth in claim 1, wherein the tubular member is made from titanium.

8. A device as set forth in claim 1, further including a spacer for partial placement within one of the sockets to permit connection of another tubular member to the spacer.

9. A device as set forth in claim 8, wherein the spacer is made from a flexible material.

10. A device as set forth in claim 8, wherein the spacer is made from a bioresorbable material.

11. A device as set forth in claim 10, wherein the bioresorbable material includes a formulation which permits relatively minimal resorption over a defined period with subsequent substantially complete resorption thereafter.

12. A device as set forth in claim 10, wherein the bioresorbable material includes poly-(L-lactide), poly-(DL-lactide), polyglycolide, or a combination thereof.

13. A device as set forth in claim 1, wherein the radioactive source is a substantially elongated segment.

14. A device as set forth in claim 13, wherein the radioactive source includes one of $^{125}$Iodine, $^{103}$Palladium, $^{137}$Cesium, and $^{192}$Iridium.

15. An assembly for radiation therapy comprising:
a plurality of tubular members, each having opposing ends, and a central section positioned between the opposing ends;
a radioactive source positioned within the tubular member at the central section; and
a socket at each of the opposing ends, the sockets being defined by a difference in length between a tubular member and the radioactive source therein; and
a spacer positioned between two tubular members, such that the spacer is partially retained within one socket of each tubular member, to permit joining of the tubular members in series along a common axis.

16. An assembly as set forth in claim 15, further including a spacer partially positioned within a distal most socket of a distal most tubular member in the series.

17. A method for manufacturing a brachytherapy implant, the method comprising:
providing a tubular member having opposing ends and a central section between the opposing ends;
placing within the member a sealed radioactive source having a length relatively shorter than that of the member, such that the difference in length between the radioactive source and the tubular member defines a socket at each of the opposing ends of the tubular member and at least one of the sockets is open to the sealed radioactive source; and
positioning a spacer within a socket.

18. A method for manufacturing a brachytherapy implant, the method comprising:
providing a tubular member having opposing ends and a central section between the opposing ends;
placing within the member a radioactive source having a length relatively shorter than that of the member, such that the difference in length between the radioactive source and the tubular member defines a socket at each of the opposing ends of the tubular member.
placing a spacer into one of the opposing sockets; and
securing the spacer into the socket.

19. A method for manufacturing a brachytherapy implant, the method comprising:
providing a first tubular member having opposing ends and a central section between the opposing ends;
placing within the first tubular member a radioactive source having a length relatively shorter than that of the first tubular member, such that the difference in length between the radioactive source and the first tubular member defines a socket at each of the opposing ends of the tubular member;
positioning a spacer within a socket of the first tubular member;
providing a second tubular member having opposing ends and a central section between the opposing ends;
placing within the second member a radioactive source having a length relatively shorter than that of the second member, such that the difference in length between the radioactive source and the second member defines a socket at each of the opposing ends of the second member;
positioning one of the sockets in the second member on to the spacer in the socket of the first tubular member; and
securing the spacer to the socket of the second member.

20. A method for treating pathological tissues, the method comprising:
identifying a site having pathological tissues;
providing an implantable device comprising at least one substantially tubular member having opposing ends, a central section positioned between the opposing ends, a radioactive source positioned at the central section, such that a socket is defined at each of the opposing ends by the difference in length between the radioactive source and the tubular member;
positioning the implantable device within a lumen of delivery mechanism;
inserting the delivery mechanism at the site having the pathological tissues to a depth which permits access to the pathological tissues; and
delivering the implantable device from the lumen of the delivery mechanism to the site of pathological tissues.

21. A method as set forth in claim 20, wherein the step of providing further includes:
securing a spacer within one of the opposing sockets; and
attaching the spacer to a socket of a second implantable device.

22. A method for treating pathological tissues, the method comprising:
providing an implantable device comprising at least one substantially tubular member having opposing ends, a central section positioned between the opposing ends, a radioactive source positioned at the central section, such that a socket is defined at each of the opposing ends by the difference in length between the radioactive source and the tubular member;
surgically exposing a site having pathological tissues;
positioning the implantable device within the exposed site; and
closing the exposed site to retain the implantable device therein.

23. A method as set forth in claim 22, wherein the step of providing further includes:
securing a spacer within one of the opposing sockets; and
attaching the spacer to a socket of a second implantable device.

24. An implantable device for radiation therapy, comprising:
first and second substantially tubular members having opposing ends and a central section positioned between the opposing end;
first and second radioactive sources positioned within the first and second members, respectively, at the central section;
a socket at each of the opposing ends of each substantially tubular member, the sockets being defined by a difference in length between the substantially tubular member and the radioactive source; and
a spacer having first and second ends, the first end secured in a socket of the first substantially tubular member and the second end secured in a socket of the second tubular member.

* * * * *